(12) United States Patent
Kaneko et al.

(10) Patent No.: US 11,923,072 B2
(45) Date of Patent: Mar. 5, 2024

(54) IMAGE DIAGNOSIS SUPPORTING DEVICE AND IMAGE PROCESSING METHOD

(71) Applicant: Hitachi, Ltd., Tokyo (JP)

(72) Inventors: Yukio Kaneko, Tokyo (JP); Yun Li, Tokyo (JP); Zisheng Li, Tokyo (JP); Aya Kishimoto, Tokyo (JP); Kazuki Matsuzaki, Tokyo (JP); Peifei Zhu, Tokyo (JP); Masahiro Ogino, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 365 days.

(21) Appl. No.: 17/197,445

(22) Filed: Mar. 10, 2021

(65) Prior Publication Data

US 2022/0101983 A1 Mar. 31, 2022

(30) Foreign Application Priority Data

Sep. 28, 2020 (JP) .................................. 2020-162039

(51) Int. Cl.
| | | |
|---|---|---|
| *G16H 30/40* | (2018.01) | |
| *G06T 5/40* | (2006.01) | |
| *G06T 7/00* | (2017.01) | |
| *G16H 50/20* | (2018.01) | |

(52) U.S. Cl.
CPC .............. *G16H 30/40* (2018.01); *G06T 5/40* (2013.01); *G06T 7/0012* (2013.01); *G16H 50/20* (2018.01); *G06T 2207/20081* (2013.01); *G06T 2207/30096* (2013.01)

(58) Field of Classification Search
CPC ...................... G06T 5/40; G06T 7/0012; G06T 2207/20081; G06T 2207/20084; G06T 2207/10081; G06T 2207/10116; G06T 7/00; G06T 2207/30096; G06T 3/0093; G06T 2207/10088; G06T 2207/30004; G06T 3/4084; G16H 30/40; G06V 10/758;

(Continued)

(56) References Cited

U.S. PATENT DOCUMENTS

| | | | |
|---|---|---|---|
| 6,984,211 B2* | 1/2006 | Hao | G06T 7/12 600/443 |
| 7,430,308 B1* | 9/2008 | Kallergi | G06T 7/0012 382/128 |
| 10,354,171 B2* | 7/2019 | Hsieh | G06F 18/2193 |

(Continued)

FOREIGN PATENT DOCUMENTS

| | | |
|---|---|---|
| JP | 2019-097805 A | 6/2019 |
| JP | 2020-89710 A | 6/2020 |
| JP | 2020-98444 A | 6/2020 |

OTHER PUBLICATIONS

Japanese Office Action received in corresponding Japanese Application No. 2020-162039 dated Dec. 26, 2023.

*Primary Examiner* — John Villecco
*Assistant Examiner* — Courtney Joan Nelson
(74) *Attorney, Agent, or Firm* — Mattingly & Malur, PC

(57) ABSTRACT

An image diagnosis supporting device includes a model reader that reads an image diagnostic model that outputs a diagnostic result for a diagnostic image that is an input medical image, a storage unit that stores facility data that is a plurality of medical images associated with diagnostic results held in a facility, and an adjuster that adjusts, based on the facility data, the image diagnostic model or the diagnostic image input to the image diagnostic model.

10 Claims, 9 Drawing Sheets

(58) Field of Classification Search
CPC . G06V 10/454; G06V 2201/031; H04N 19/59
See application file for complete search history.

(56) References Cited

U.S. PATENT DOCUMENTS

2020/0192609 A1   6/2020  Shinkai
2020/0381115 A1*  12/2020 Kikuchi ................ G16H 30/40

* cited by examiner

FIG. 6
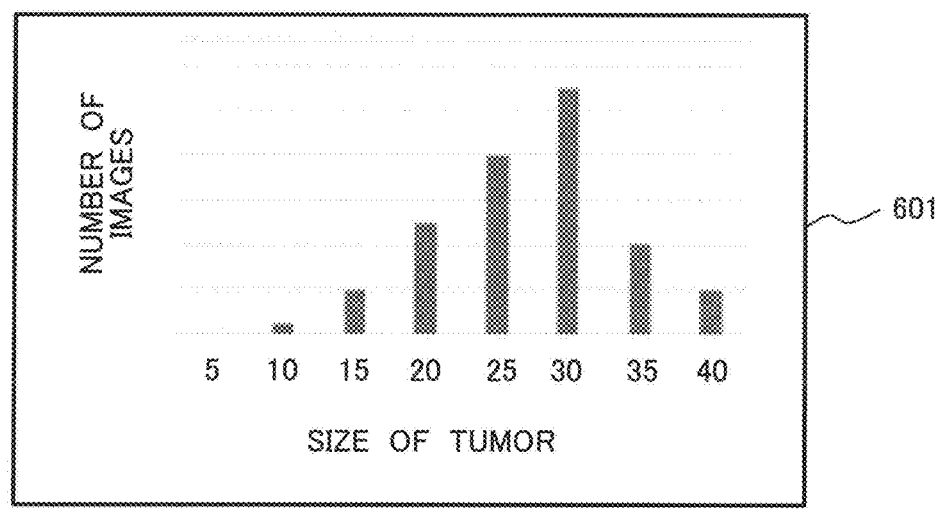
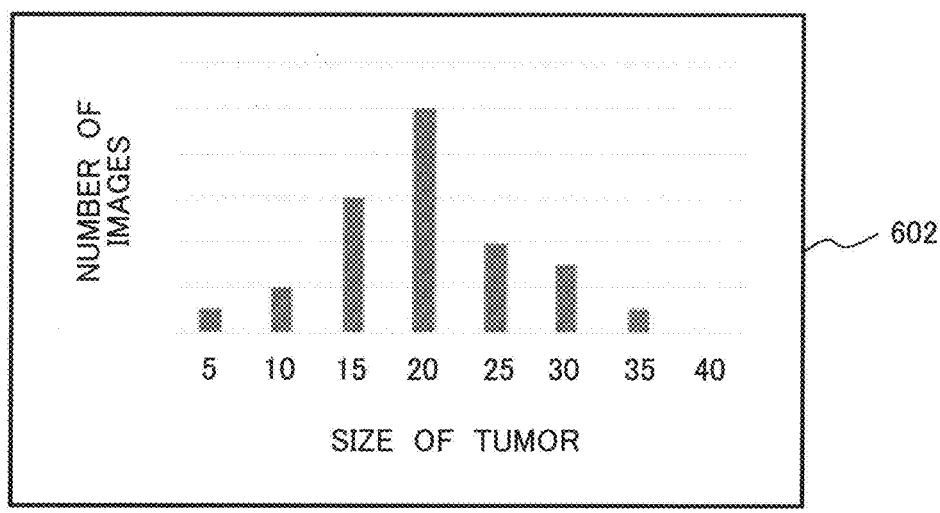

FIG. 8
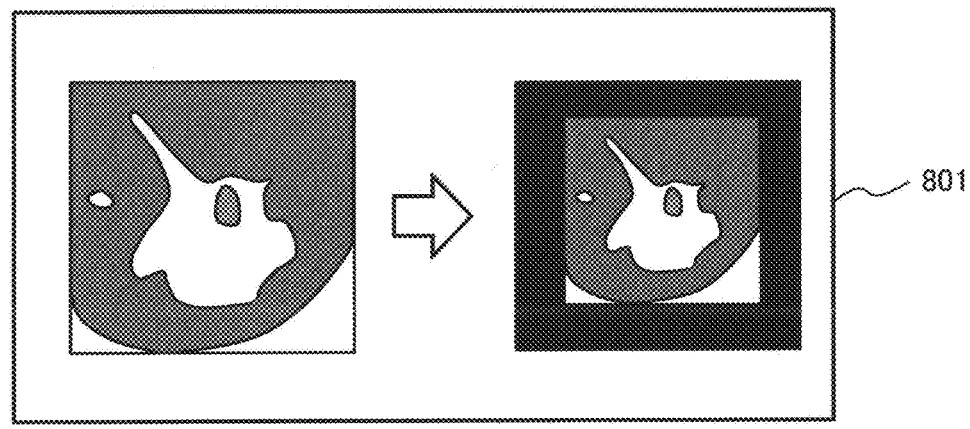
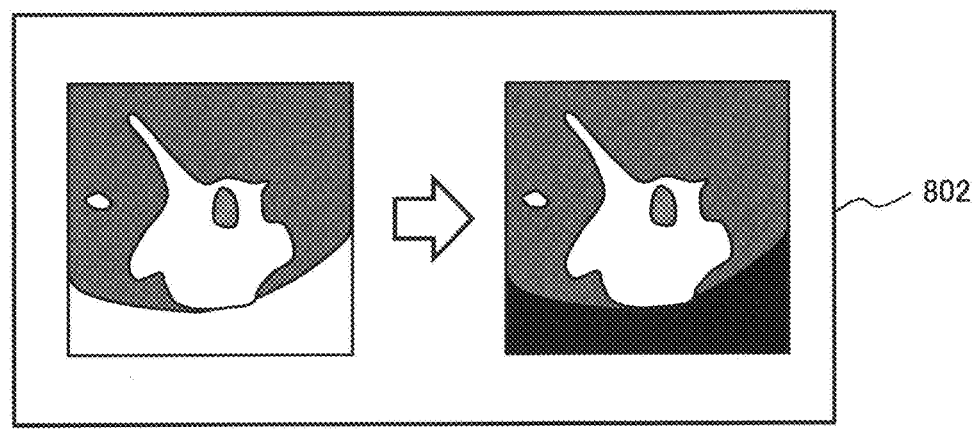

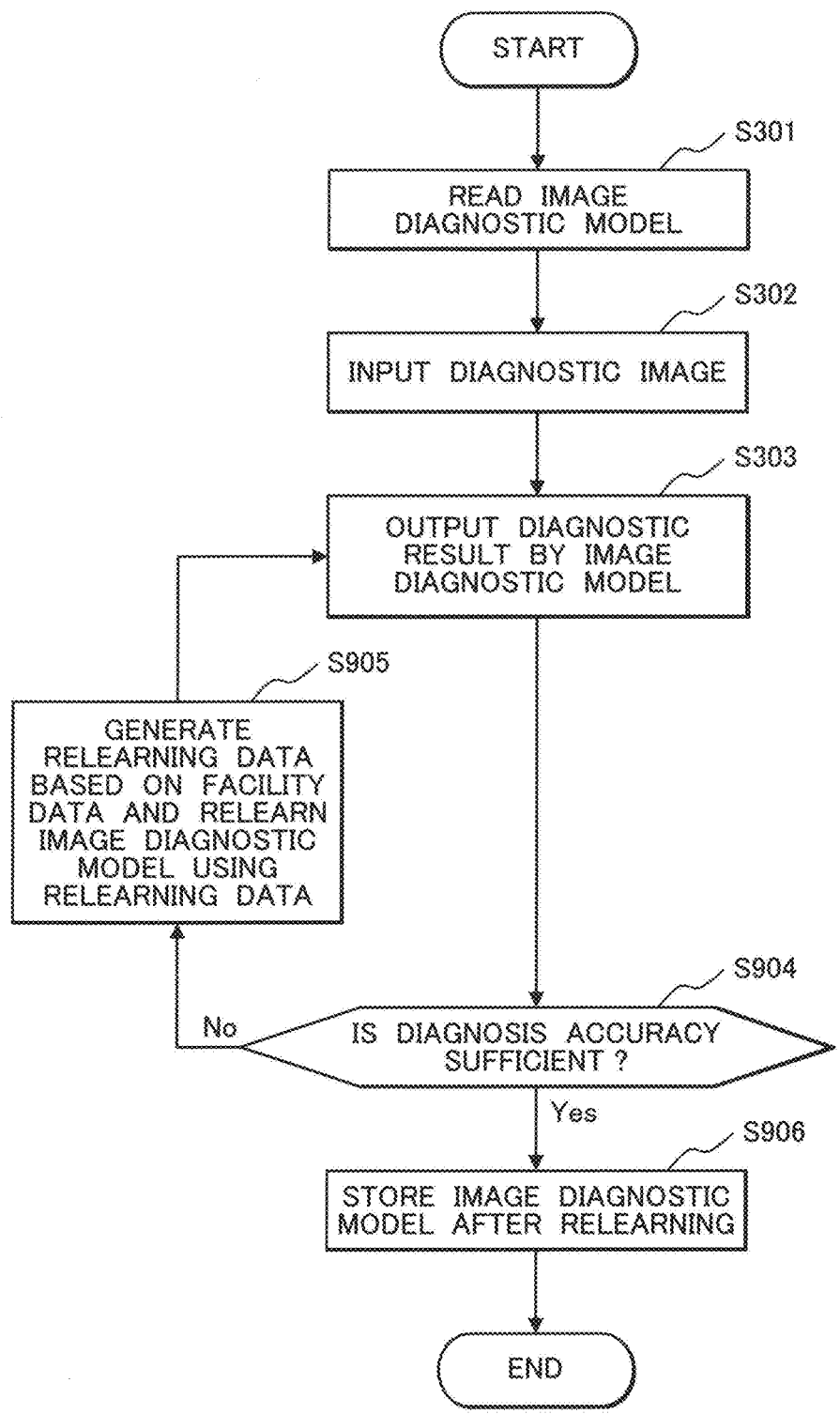

IMAGE DIAGNOSIS SUPPORTING DEVICE AND IMAGE PROCESSING METHOD

CLAIM OF PRIORITY

The present application claims priority from Japanese Patent Application JP 2020-162039 filed on Sep. 28, 2020, the content of which are hereby incorporated by references into this application.

BACKGROUND OF THE INVENTION

The present invention relates to an image diagnosis supporting device and an image processing method that use artificial intelligence or the like to support diagnosis of a lesion included in a medical image acquired by a medical image acquiring device, and particularly to a technique for improving diagnosis accuracy.

A medical image acquiring device represented by an X-ray computed tomography (CT) device or the like images the shape of a portion such as a lesion. The lesion included in a medical image is diagnosed by a radiologist. To reduce an increased burden on radiologists that has been caused by higher performance of medical image acquiring devices, an image diagnosis supporting device that diagnoses a lesion by artificial intelligence (AI) has been developed in recent years. Many image diagnosis supporting devices have only estimated a disease name from a medical image based on many image characteristic amounts that are values indicating characteristics of a medical image, and doctors have not been able to determine whether a result of the estimation is useful for diagnosis.

Japanese Unexamined Patent Application Publication No. 2019-97805 discloses an information processing device that uses an image diagnostic model, which has been subjected to machine learning to estimate a disease name from a medical image, to estimate a disease name from a medical image, and presents, as reference information, image findings that highly affect a result of estimating the disease name. Specifically, the disease name and the image findings representing characteristics of the medical image are estimated based on each of image characteristic amounts of the medical image. The image findings that are affected by image characteristic amounts common to image characteristic amounts affecting the result of estimating the disease name and are estimated are presented as the reference information.

SUMMARY OF THE INVENTION

However, according to Japanese Unexamined Patent Application Publication No. 2019-97805, since the existing image diagnostic model is used to execute image diagnosis, a diagnostic result may not be appropriate for each facility. Specifically, diagnosis accuracy may not be sufficient due to a difference between characteristics of facilities such as a difference between characteristics of patients, a difference between types of image diagnostic devices, or the like.

Therefore, an object of the present invention is to provide an image diagnosis supporting device and an image processing method that use an existing image diagnostic model to acquire a diagnostic result appropriate for each facility.

To achieve the foregoing object, according to an aspect of the present invention, an image diagnosis supporting device includes a model reader that reads an image diagnostic model that outputs a diagnostic result for an input diagnostic image, a storage unit that stores facility data that is a plurality of medical images associated with diagnostic results held in a facility, and an adjuster that adjusts, based on the facility data, the image diagnostic model or the diagnostic image input to the image diagnostic model.

According to another aspect of the present invention, an image processing method causes a computer to execute a process including the steps of reading an image diagnostic model that outputs a diagnostic result for a diagnostic image that is an input medical image, and adjusting, based on facility data that is a plurality of medical images associated with diagnostic results held in a facility, the image diagnostic model or the diagnostic image input to the image diagnostic model.

According to the present invention, it is possible to provide an image diagnosis supporting device and an image processing method that use an existing image diagnostic model to acquire a diagnostic result appropriate for each facility.

BRIEF DESCRIPTION OF THE DRAWINGS

FIG. 6 is a diagram illustrating an example of a result of executing a statistical process on facility data;

FIG. 8 is a diagram illustrating an example of adjustment of a diagnostic image; and FIG. 9 is a diagram illustrating an example of a process procedure according to a second embodiment.

DETAILED DESCRIPTION OF THE PREFERRED EMBODIMENTS

Hereinafter, preferable embodiments of an image diagnosis supporting device according to the present invention and an image processing device according to the present invention are described with reference to the accompanying drawings. In the following description and the accompanying drawings, constituent components that have the same functional configurations are indicated by the same reference signs, and thus duplicate descriptions are omitted.

First Embodiment

Figure 1:
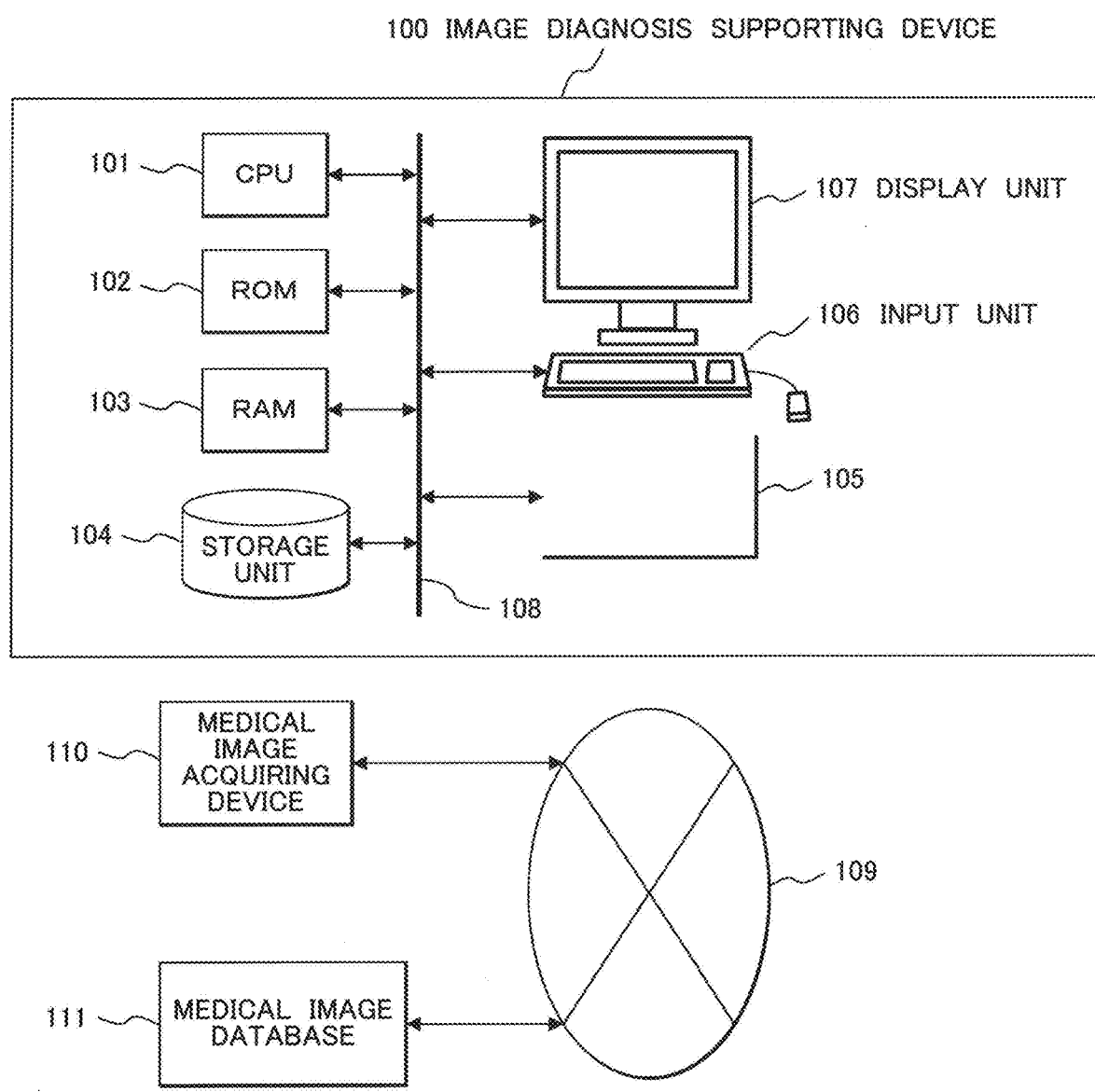
FIG. 1 is a hardware configuration diagram of an image diagnosis supporting device according to a first embodiment.

A hardware configuration of an image diagnosis supporting device 100 according to a first embodiment is described with reference to FIG. 1. The image diagnosis supporting device 100 is a computer. Specifically, the imager diagnosis supporting device 100 includes a central processing unit (CPU) 101, a read-only memory 102 (ROM), a random-access memory (RAM) 103, a storage unit 104, a network adapter 105, an input unit 106, and a display unit 107 that are connected to each other via a bus 108 and able to transmit and receive a signal to and from each other via the bus 108. The image diagnosis supporting device 100 is connected to a medical image acquiring device 110 and a medical image database 111 via the network adapter 105 and a network 109 and able to transmit and receive a signal to and from the medical image acquiring device 110 and the medical image database 111 via the network adapter 105 and the network 109. In this case, the term "able to transmit and receive" indicates a state in which each of the units 101 to 107 is able to electrically or optically transmit and/or receive a signal to and/or from the other units via a cable or wirelessly and a state in which the image diagnosis supporting device 100 can electrically or optically transmit and/or receive a signal to and/or from the medical image acquiring device 110 and the medical image database 111 via a cable or wirelessly.

The CPU 101 is a device that reads a system program stored in the ROM 102 or the like and controls operations of the constituent units. The CPU 101 loads a program stored in the storage unit 104 and data necessary to execute the program into the RAM 103 and executes the program. The storage unit 104 is a device that stores the program to be executed by the CPU 101 and the data necessary to execute the program. Specifically, the storage unit 104 is a storage device such as a hard disk drive (HDD) or a solid state drive (SSD), or is a device that reads and writes data from and to a recording medium such as an IC card, an SD card, or a DVD. Various data including the data necessary to execute the program is transmitted from the network 109 such as a local area network (LAN), and received. In the RAM 103, the program to be executed by the CPU 101, information indicating the progress of arithmetic processing, and the like are stored.

The display unit 107 is a device that displays a result of executing the program and the like. The display unit 107 is a liquid crystal display, a touch panel, or the like. The input unit 106 is an operation device to be used by an operator to give an operation instruction to the image diagnosis supporting device 100. The input unit 106 is a keyboard, a mouse, or the like. The mouse may be replaced with another pointing device such as a track pad or a track ball. When the display unit 107 is a touch panel, the touch panel also functions as the input unit 106. The network adapter 105 connects the image diagnosis supporting device 100 to the network 109 such as the LAN, a phone line, or the Internet.

The medical image acquiring device 110 acquires a medical image such as a tomographic image acquired by imaging the shape of a portion such as a lesion. The medical image acquiring device 110 is an X-ray imaging device, an X-ray computed tomography (CT) device, a magnetic resonance imaging (MRI) device, an ultrasonic diagnostic device, or the like. The medical image acquiring device 110 may generate a three-dimensional medical image by stacking a plurality of tomographic images. The medical image database 111 is a database system that stores a medical image acquired by the medical image acquiring device 110.

Figure 2:
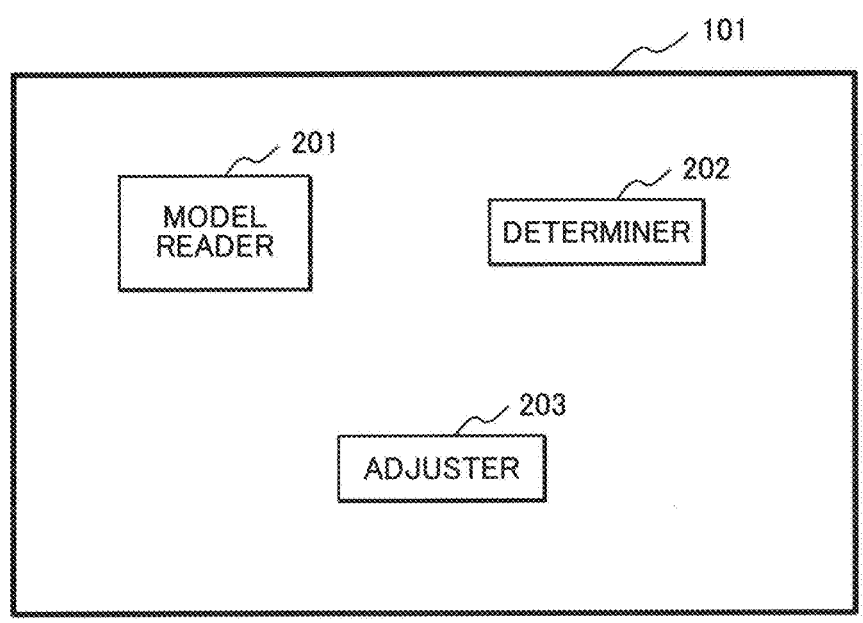
FIG. 2 is a functional block diagram according to the first embodiment.

A functional block diagram according to the first embodiment is described with reference to FIG. 2. Functions according to the first embodiment may be configured as dedicated hardware with an application specific integrated circuit (ASIC), a field-programmable gate array (FPGA), or the like or may be configured as software to be executed on the CPU 101. The following describes the case where the functions are configured as the software. In the first embodiment, the image diagnosis supporting device 100 includes a model reader 201, a determiner 202, and an adjuster 203. The functions 201 to 203 are described below.

The model reader 201 reads, from the storage unit 104 or from the Internet or the like via the network adapter 105, an image diagnostic model that outputs a diagnostic result for an input medical image. The image diagnostic model is an existing program built with a random forest, a support-vector machine (SVM), a layered neural network, or the like. The image diagnostic model is an arbitrary program in which a processing algorithm is described as a black-boxed algorithm. A medical image input to the image diagnostic model may be an arbitrary image or may be, for example, a two- or three-dimensional medical image or a certain region of a medical image. A diagnostic result output from the image diagnostic model is, for example, a result of determining whether a lesion is benign or malignant. The diagnostic result is a probability that the lesion is malignant or the like.

The determiner 202 determines whether the diagnostic result output from the image diagnostic model is sufficient as diagnosis accuracy. A threshold that is defined for each facility is used for the determination by the determiner 202. When the determiner 202 determines that the diagnostic result is not sufficient as the diagnosis accuracy, the adjuster 203 operates. The determiner 202 may not be an essential function. The adjuster 203 may operate even when the determiner 202 does not make the determination.

The adjuster 203 adjusts a diagnostic image input to the image diagnostic model based on facility data that is a plurality of medical images associated with diagnostic results held in a facility. Specifically, to improve the accuracy of a diagnostic result output from the image diagnostic model, the adjuster 203 increases or reduces a size of the diagnostic image or deletes an arbitrary region included in the diagnostic image. The adjustment is described later in detail with reference to FIG. 8.

Figure 3:
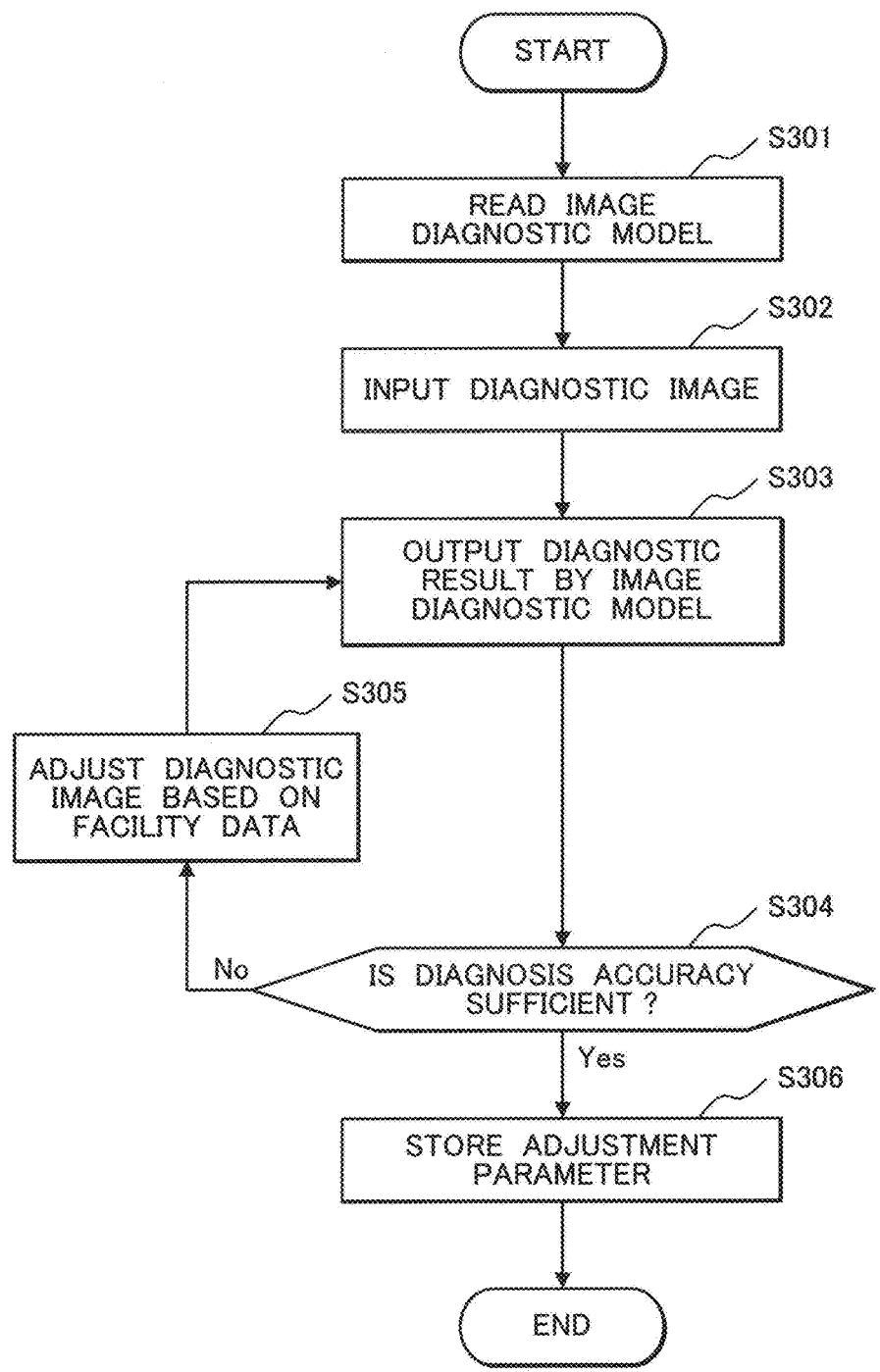
FIG. 3 is a diagram illustrating an example of a process procedure according to the first embodiment.

An example of a process procedure according to the first embodiment is described with reference to FIG. 3.

In S301, the model reader 201 reads the image diagnostic model from the storage unit 104 or from the Internet or the like via the network adapter 105.

In S302, a diagnostic image that is a medical image targeted for diagnosis is input to the image diagnostic model. The diagnostic image is read from a radiology information system (RIS) included in the facility or the like.

In S303, the image diagnostic model outputs, as a diagnostic result for the diagnostic image input in S302, a probability that a tumor included in the diagnostic image is malignant, for example. The image diagnostic model may output not only the diagnostic result but also a degree of importance for each of evaluation regions. The evaluation regions are regions extracted from the diagnostic image as regions that affect the diagnostic result. The degrees of importance for the evaluation regions are values indicating degrees at which the plurality of evaluation regions affect the diagnostic result. The degrees of importance for the evaluation regions are indicated and thus the operator can confirm an evaluation region largely affecting the diagnostic result or an evaluation region on which the diagnosis is based.

Figure 4:
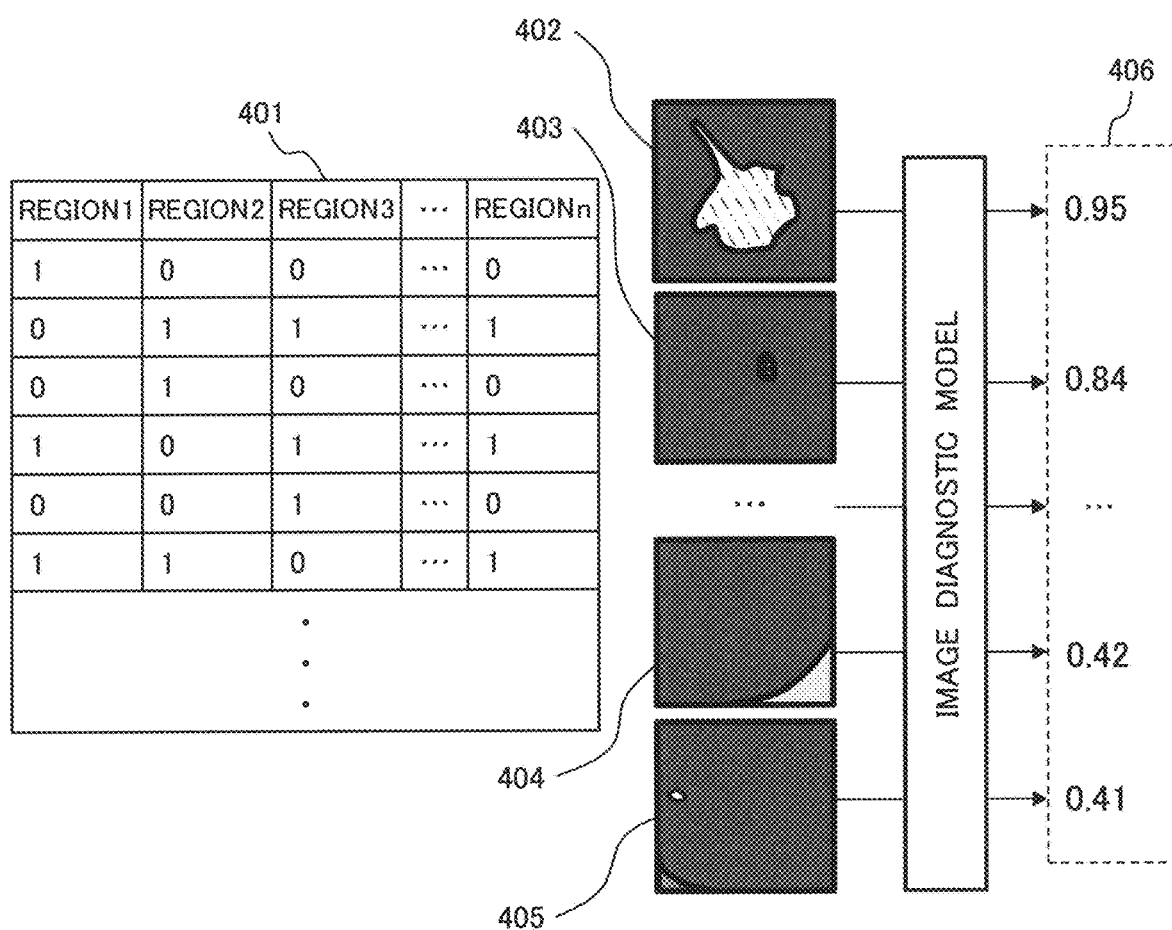
FIG. 4 is a diagram describing calculation of a degree of importance for each evaluation region.

An example of calculation of the degrees of importance for the evaluation regions is described with reference to FIG. 4. The evaluation regions that affect the diagnostic result are extracted based on a diagnosis guideline in which the basis for the diagnosis and a procedure for the diagnosis are described or the like. For example, in the determination of whether a lung tumor is benign or malignant, a lung tumor region, an aeration region, a chest wall region, a blood vessel region, and the like are extracted as evaluation regions based on a guideline for lung cancer diagnosis or the like.

The extracted evaluation regions are input to the image diagnostic model as images indicating distribution information of luminance values. The degrees of importance are calculated for the respective evaluation regions. Specifically, the degrees of importance are calculated for the respective evaluation regions based on combinations of the evaluation regions and diagnostic results obtained by inputting various combinations of the evaluation regions to the image diagnostic model. The combinations of the evaluation regions are indicated in, for example, a sampling table 401.

The sampling table 401 is composed of an item row indicating n extracted evaluation regions and a sampling matrix. Whether the evaluation regions are included in images associated with rows are indicated by values of matrix elements of the sampling matrix. Specifically, when a value of each of the rows is 1, a corresponding evaluation region is included in an image associated with the row. An evaluation region of a column indicating a value of 0 is not included in an image associated with a row indicating the value of 0. For the evaluation region that is not included in the image associated with the row, a luminance value of 0 is set. Alternatively, the evaluation region that is not included in the image associated with the row is filled with a black color. For example, for an image associated with the first row, a value of a region 1 is 1 and values of regions 2 to n are 0. Thus, only the region 1 is included in the image associated with the first row. When the region 1 is a lung tumor region, the concerned image is a lung tumor region image 402 including only the lung tumor region. For an image associated with the second row, a value of the region 1 is 0 and values of the regions 2 to n are 1. Thus, only the region 1 is not included in the image associated with the second row.

The size of the sampling matrix is determined based on the number n of evaluation regions and a number m of combinations of the evaluation regions. Specifically, the sampling matrix is a matrix of m rows and n columns. It is preferable that the number m of combinations of the evaluation regions be $2^n$ that is equal to the number of all combinations of the n evaluation regions in order to improve the accuracy of calculating the degrees of importance. However, the number m of combinations of the evaluation regions is not limited to $2^n$. For example, the m combinations of the evaluation regions may be equal to the n evaluation regions in such a manner that each of the combinations of the evaluation regions includes a respective one of the evaluation regions.

After images for the respective combinations of the evaluation regions indicated in the sampling matrix or the like are input to the image diagnostic model, diagnostic results for the respective combinations are output. FIG. 4 exemplifies diagnostic results 406 output by inputting, to the image diagnostic model, a lung tumor region image 402 including only a lung tumor region, an aeration region image 403 including only an aeration region, a chest wall region image 404 including only a chest wall region, and a blood vessel region image 405 including only a blood vessel region. According to the diagnostic results 406 illustrated in FIG. 4, as degrees of importance for the respective evaluation regions, 0.95 is output for the lung tumor region image 402, 0.84 is output for the aeration region image 403, 0.42 is output for the chest wall region image 404, and 0.41 is output for the blood vessel region image 405. From the results exemplified in FIG. 4, the operator can confirm that the lung tumor region and the aeration region are more important as the basis for the diagnostic result than the chest wall region and the blood vessel region.

Figure 5:
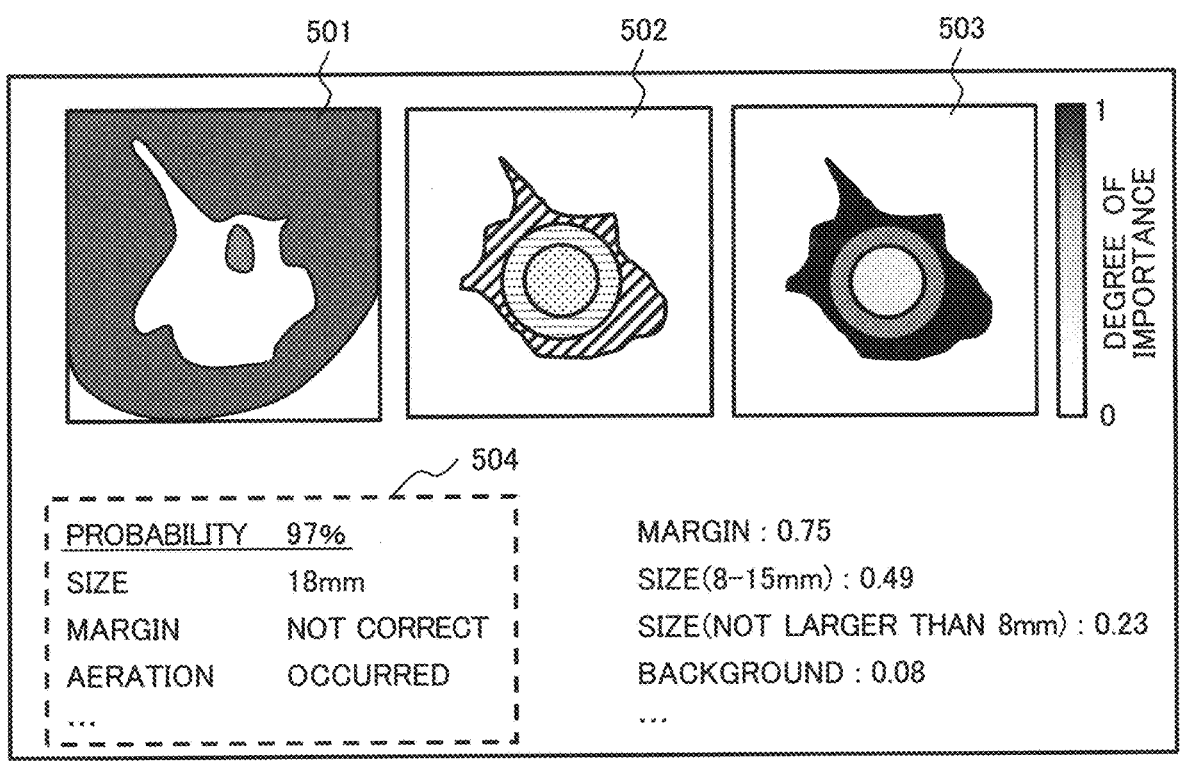
FIG. 5 is a diagram illustrating an example of a display screen for a diagnostic result and a degree of importance.

An example of a screen displayed in S303 is described with reference to FIG. 5. A screen illustrated in FIG. 5 includes a diagnostic image display section 501, an evaluation region display section 502, a degree-of-importance display section 503, and a diagnostic result display section 504. In the diagnostic image display section 501, an image of a lung tumor region that is a region including a tumor within a diagnostic image is displayed. In the evaluation region display section 502, results of dividing the image displayed in the diagnostic image display section 501 into a plurality of evaluation regions are displayed. In the degree-of-importance display section 503, an image in which the degrees of importance that are calculated for the respective evaluation regions are visualized is displayed. In the diagnostic result display section 504, a probability of 97% that a tumor that is a diagnostic result is malignant, the size of the tumor, a property of the tumor margin, information indicating whether aeration has occurred, and the like are displayed.

In S304, the determiner 202 determines, based on the diagnostic result output in S303, whether the accuracy of diagnosis by the image diagnostic model is sufficient. When the accuracy of the diagnosis is not sufficient, the process returns to S303 via S305. When the accuracy of the diagnosis is sufficient, the process proceeds to S306. Thresholds defined for respective facilities are used to determine the accuracy of the diagnosis. For example, when a probability that the tumor that is the diagnostic result is malignant is lower than a threshold, the determiner 202 determines that the accuracy of the diagnosis is not sufficient. Values of probabilities that diagnostic results are correct are set as the thresholds defined for the respective facilities.

In S305, the adjuster 203 adjusts the diagnostic image based on the facility data. After the diagnostic image is adjusted, the process returns to S303 and the image diagnostic model outputs a diagnostic result for the diagnostic image after the adjustment. For example, the diagnostic image is adjusted based on a result of executing a statistical process on the facility data.

An example of the result of executing the statistical process on the facility data is described with reference to FIG. 6. FIG. 6 illustrates a facility histogram 601 and a teacher histogram 602. The facility histogram 601 is generated using each of the medical images of the facility data. FIG. 6 illustrates the facility histogram 601 in which the abscissa indicates sizes of tumors included in the medical images. The teacher histogram 602 is generated using teacher data used to generate the image diagnostic model. In the teacher histogram 602, the abscissa indicates sizes of tumors included in medical images in the same manner as the facility histogram 601. The teacher data is a plurality of medical images different from the facility data. Diagnostic results are associated with the respective medical images. The statistical process may not be executed on the facility data in such a manner that the histogram in which the abscissa indicates the sizes of the tumors is generated. The statistical process may be executed using an item selected by the operator.

Figure 7:
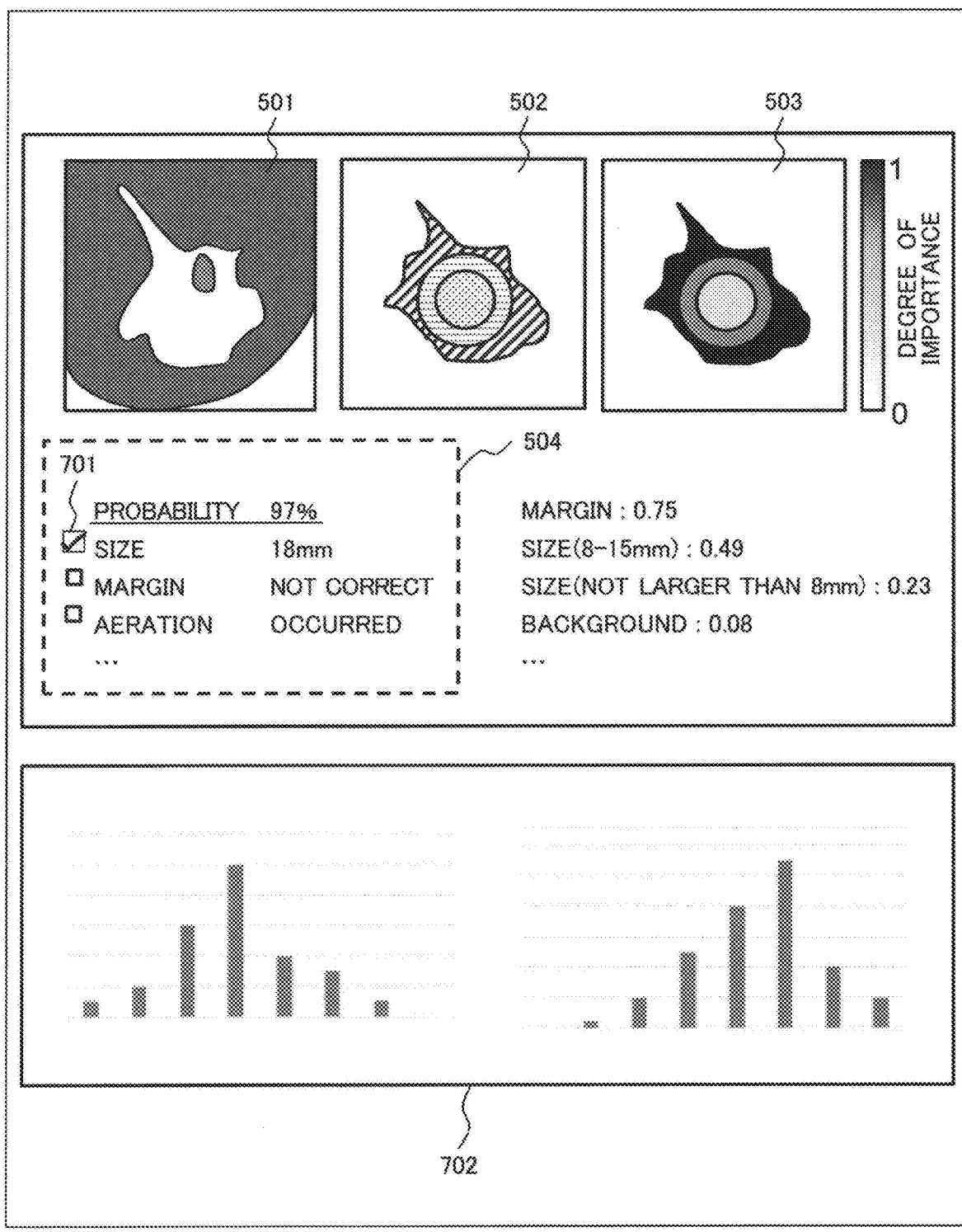
FIG. 7 is a diagram illustrating an example of a screen for selecting an item to be used for the statistical process.

An example of a screen for selecting an item to be used for the statistical process to be executed on the facility data is described with reference to FIG. 7. A screen illustrated in FIG. 7 includes the diagnostic image display section 501, the evaluation region display section 502, the degree-of-importance display section 503, the diagnostic result display section 504, an item selection section 701, and a statistical result display section 702. The display sections 501 to 504 are described above with reference to FIG. 5. The item selection section 701 is checkboxes, each of which is used by the operator to select an item to be used for the statistical process. An item associated with a selected checkbox is used for the statistical process. The operator can select a desired item from the item selection section 701 to improve the accuracy of the diagnosis from the viewpoint that the operator places importance on the selected item.

In the statistical result display section 702, a result of the statistical process executed using the item selected from the item selection section 701 is displayed. In the statistical result display section 702, not only the result of executing the statistical process on the facility data but also a result of executing the statistical process on the teacher data may be displayed. Displaying both the facility data and the teacher data in comparison to each other clarifies whether a characteristic of the facility is appropriate for the image diagnostic model. For example, by comparing the facility histogram 601 illustrated in FIG. 6 with the teacher histogram 602 illustrated in FIG. 6, it is found that a distribution of the sizes of the tumors in the facility data is different from a distribution of the sizes of the tumors in the teacher data and that the characteristic of the facility is not appropriate for the image diagnostic model. The adjuster 203 may adjust the diagnostic image to reduce the difference between the facility data and the teacher data in order to make the characteristic of the facility appropriate for the image diagnostic model. For example, the adjuster 203 adjusts the size of the diagnostic image based on a difference between a mode value of the facility histogram 601 and a mode value of the teacher histogram 602.

An example of the adjustment of the diagnostic image is described with reference to FIG. 8. FIG. 8 illustrates a first adjustment example 801 and a second adjustment example 802. The first adjustment example 801 is an example in which the size of the diagnostic image is reduced based on the comparison of the facility histogram 601 with the teacher histogram 602. Specifically, in the first adjustment example 801, when the mode value of the facility histogram 601 is 30 mm and the mode value of the teacher histogram 602 is 20 mm, each of sides of the diagnostic image is multiplied by ⅔ in such a manner that the diagnostic image is reduced in size. The second adjustment example 802 is an example in which a high-luminance region present near a tumor is removed. Specifically, the second adjustment example 802 is the example in which the high-luminance region is removed by filling, with a black color, a chest wall region that is the high-luminance region present on the lower side of the tumor.

In S306, the adjuster 203 causes an adjustment parameter relating to the adjustment of the diagnostic image in S305 to be stored in the storage unit 104. For example, when the diagnostic image is reduced in size by multiplying each of the sides of the diagnostic image by ⅔, ⅔ is stored as the adjustment parameter. When the process reaches S306 without the execution of the process of S305, the adjustment parameter may not be stored. When the process reaches S306, the diagnostic result appropriate for the facility has been acquired in S303.

Since the diagnostic image is adjusted by the foregoing process procedure in such a manner that the characteristic of the facility is appropriate for the image diagnostic model, it is possible to use an existing image diagnostic model to acquire diagnostic results appropriate for respective facilities. In the process procedure illustrated in FIG. 3, the determination process of S304 may not be included. When the determination process of S304 is not included, it is sufficient if the image diagnostic model outputs a diagnostic result for the diagnostic image subjected to the adjustment process of S305 in S303.

Second Embodiment

The first embodiment describes the case where the diagnostic image input to the image diagnostic model is adjusted based on the facility data. To improve the diagnosis accuracy, the image diagnostic model may be adjusted by relearning, in addition to the adjustment of the diagnostic image input to the image diagnostic model. A second embodiment describes the case where relearning data that is used to adjust the image diagnostic model is generated based on the facility data and the image diagnostic model is adjusted using the relearning data. A whole configuration according to the second embodiment is the same as that according to the first embodiment and will not be described below. Although a functional block diagram according to the second embodiment is the same as that according to the first embodiment, an operation of an adjuster 203 according to the second embodiment is different from that according to the first embodiment. Therefore, the adjuster 203 is described below.

The adjuster 203 according to the second embodiment generates the relearning data based on the facility data that is the plurality of medical images associated with the diagnostic results held in the facility. The relearning data is used to adjust the image diagnostic model. The image diagnostic model is relearned using the generated relearning data and adjusted in such a manner that the accuracy of a diagnostic result is improved.

An example of a process procedure according to the second embodiment is described with reference to FIG. 9. S301, S302, and S303 of the process procedure according to the second embodiment are the same processes as those described in the first embodiment and will be described briefly.

In S301, the model reader 201 reads the image diagnostic model.

In S302, a diagnostic image is input to the image diagnostic model

In S303, the image diagnostic model outputs a diagnostic result for the diagnostic image.

In S904, the determiner 202 determines, based on the diagnostic result output in S303, whether the accuracy of diagnosis by the image diagnostic model is sufficient. When the accuracy of the diagnosis is not sufficient, the process returns to S303 via S905. When the accuracy of the diagnosis is sufficient, the process proceeds to a process of S906.

In S905, the adjuster 203 generates the relearning data based on the facility data and adjusts the image diagnostic model using the generated relearning data. After the image diagnostic model is adjusted, the process returns to the process of S303 and the image diagnostic model after the adjustment outputs a diagnostic result for the diagnostic image.

Some examples of the relearning data are described below. It is desirable that a characteristic of the facility data be reflected in the relearning data in such a manner that a diagnostic result appropriate for the facility can be acquired. Thus, the facility data may be used as the relearning data.

When the number of images included in the facility data is significantly smaller than the number of images included in the teacher data used to generate the image diagnostic model, it may not be possible to obtain sufficient diagnosis accuracy due to insufficiency of a learning amount. In this case, the relearning data may be generated by adding the teacher data to the facility data in such a manner that the relearning data does not cause the learning amount to be insufficient.

However, when a characteristic of the teacher data to be added is significantly different from the characteristic of the facility data, it is difficult to acquire a diagnostic result appropriate for the facility. Thus, the relearning data may be generated by extracting data close to the characteristic of the facility data from the teacher data and adding the extracted data to the facility data. For example, a probability function calculated from the facility histogram 601 exemplified in FIG. 6 may be used to extract, from the teacher data, data to be added to the facility data. The probability function is calculated by fitting the facility histogram 601. A distribution of the data extracted from the teacher data using the probability function is similar to the facility histogram 601 and is data close to the characteristic of the facility data. Therefore, the image diagnostic model adjusted by relearning the generated relearning data can output a diagnostic result appropriate for the facility.

In S906, the adjuster 203 causes the image diagnostic model adjusted in S905 or the image diagnostic model after the relearning to be stored in the storage unit 104. When the process reaches S906 without the execution of the process of S905, the image diagnostic model after the relearning may not be stored. When the process reaches S906, the diagnostic result appropriate for the facility has been acquired in S303.

Since the image diagnostic model is adjusted to be appropriate for the characteristic of the facility in the foregoing process procedure, it is possible to use an existing image diagnostic model to acquire a diagnostic result appropriate for each facility. In the process procedure illustrated in FIG. 9, the determination process of S904 may not be included. When the determination process of S904 is not included, the image diagnostic model adjusted in S905 may output a diagnostic result for the diagnostic image in S303.

The plurality of embodiments of the present invention are described above. The present invention is not limited to the embodiments and includes various modifications. For example, the embodiments are described above in detail to clarify the present invention and are not limited to the device including all the configurations described above and the method including all the processes described above. Some of the configurations described in one of the embodiments may be replaced with any of the configurations described in the other embodiment. Furthermore, any of the configurations described in one of the embodiments may be added to any of the configurations described in the other embodiment. Another configuration may be added to, removed from, or replaced with a portion of the configurations described in each of the embodiments.

REFERENCE SIGNS LIST

100 . . . image diagnosis supporting device
101 . . . CPU
102 . . . ROM
103 . . . RAM
104 . . . storage unit
105 . . . network adapter
106 . . . input unit
107 . . . display unit
108 . . . bus
109 . . . network
110 . . . medical image acquiring device
111 . . . medical image database
201 . . . model reader
202 . . . determiner
203 . . . adjuster
401 . . . sampling table
402 . . . lung tumor region image
403 . . . aeration region image
404 . . . chest wall region image
405 . . . blood vessel region image
406 . . . diagnostic result
501 . . . diagnostic image display section
502 . . . evaluation region display section
503 . . . degree-of-importance display section
504 . . . diagnostic result display section
601 . . . facility histogram
602 . . . teacher histogram
701 . . . item selection section
702 . . . statistical result display section
801 . . . first adjustment example
802 . . . second adjustment example

What is claimed is:

1. An image diagnosis supporting device comprising:
a processor; and
a memory storing instructions, that when executed by the processor, configure the processor to:
read an image diagnostic model that outputs a diagnostic result for a diagnostic image that is an input medical image,
store facility data that is a plurality of medical images associated with diagnostic results held in a facility,
adjust, based on the facility data, the image diagnostic model or the diagnostic image input to the image diagnostic model, and
generate a facility histogram that is a histogram of a size of a tumor included in each of the medical images of the facility data, and adjust a size of the diagnostic image based on the facility histogram.

2. The image diagnosis supporting device according to claim 1,
wherein the image diagnostic model is generated by learning teacher data that is a plurality of medical images different from the facility data, and
wherein the processor is configured to generate a teacher histogram that is a histogram of a size of a tumor included in each of the medical images of the teacher data, and adjust the size of the diagnostic image based on a facility mode value that is a mode value of the facility histogram and a teacher mode value that is a mode value of the teacher histogram.

3. The image diagnosis supporting device according to claim 2,
wherein the processor is configured to multiply the size of the diagnostic image by a value obtained by dividing the teacher mode value by the facility mode value.

4. The image diagnosis supporting device according to claim 1,
wherein processor is configured to, when a high-luminance region is present near a tumor included in each of the medical images of the facility data, adjust the diagnostic image by removing the high-luminance region.

5. The image diagnosis supporting device according to claim 1,
wherein the processor is configured to adjust the image diagnostic model by relearning data that is data generated based on the facility histogram.

6. The image diagnosis supporting device according to claim 5,
wherein the image diagnostic model is generated by learning teacher data that is a plurality of medical images different from the facility data, and
wherein the processor is configured to extract the relearning data from the teacher data based on the facility histogram.

7. The image diagnosis supporting device according to claim 6, wherein the processor is configured to calculate a probability function for extracting a medical image from the teacher data based on the facility histogram and use the probability function to extract the relearning data.

8. The image diagnosis supporting device according to claim 1, wherein the processor is configured to:

determine, based on a diagnostic result of the image diagnostic model, whether the adjustment is to be executed, and upon determining the adjustment is to be executed, adjust the image diagnostic model or the diagnostic image input to the diagnostic model.

9. The image diagnosis supporting device according to claim 1, further comprising a display coupled to the processor, wherein the processor is configured to display a screen for selecting an item to be used for a statistical process to be executed on the facility data on the display.

10. An image processing method for causing a computer to execute a process, the process comprising the steps of:

reading an image diagnostic model that outputs a diagnostic result for a diagnostic image that is an input medical image;

adjusting, based on facility data that is a plurality of medical images associated with diagnostic results held in a facility, the image diagnostic model or the diagnostic image input to the image diagnostic model;

generating a facility histogram that is a histogram of a size of a tumor included in each of the medical images of the facility data, and adjusting a size of the diagnostic image based on the facility histogram.

* * * * *